(12) United States Patent
Asai et al.

(10) Patent No.: US 10,500,771 B2
(45) Date of Patent: Dec. 10, 2019

(54) NEEDLE SHAPED BODY AND METHOD FOR MANUFACTURING NEEDLE SHAPED BODY

(71) Applicant: TOPPAN PRINTING CO., LTD., Taito-ku (JP)

(72) Inventors: Ryoichi Asai, Taito-ku (JP); Tomoya Sumida, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 182 days.

(21) Appl. No.: 15/367,303

(22) Filed: Dec. 2, 2016

(65) Prior Publication Data

US 2017/0080613 A1 Mar. 23, 2017

Related U.S. Application Data

(63) Continuation of application No. PCT/JP2015/002912, filed on Jun. 10, 2015.

(30) Foreign Application Priority Data

Jun. 13, 2014 (JP) ................................. 2014-122515

(51) Int. Cl.
*B29C 43/56* (2006.01)
*A61M 37/00* (2006.01)
(Continued)

(52) U.S. Cl.
CPC .............. *B29C 43/56* (2013.01); *A61B 17/20* (2013.01); *A61K 39/02* (2013.01); *A61K 39/145* (2013.01);
(Continued)

(58) Field of Classification Search
CPC .............. A61B 17/20; A61K 2039/522; A61K 2039/5254; A61K 2039/54;
(Continued)

(56) References Cited

U.S. PATENT DOCUMENTS 3,351,059 A 11/1967 Kravitz et al.
3,905,371 A 9/1975 Stickl et al.
(Continued)

FOREIGN PATENT DOCUMENTS

BE 664696 A 9/1965
JP 2008-67982 A 3/2008
(Continued)

OTHER PUBLICATIONS

International Search Report dated Aug. 18, 2015 in PCT/JP2015/002912, filed Jun. 10, 2015.
(Continued)

*Primary Examiner* — Imani N Hayman
(74) *Attorney, Agent, or Firm* — Oblon, McClelland, Maier & Neustadt, L.L.P.

(57) ABSTRACT

A method of manufacturing a needle shaped body includes forming on a surface of a substrate a needle shaped portion having a bottomed hole that extends from a tip to the substrate, contacting the tip of the needle shaped portion with a surface of a liquid in an atmosphere at a first pressure lower than atmospheric pressure, increasing the first pressure to a second pressure while the tip is in contact with the surface of the liquid such that the liquid is filled into the bottomed hole, and freeze-drying the liquid filled in the bottomed hole.

20 Claims, 6 Drawing Sheets

(51) Int. Cl.
- *A61B 17/20* (2006.01)
- *A61K 39/02* (2006.01)
- *A61K 39/145* (2006.01)
- *A61K 47/26* (2006.01)
- *B29C 43/02* (2006.01)
- *B29C 43/52* (2006.01)
- *C12N 7/00* (2006.01)
- *A61K 39/00* (2006.01)
- *B29L 31/00* (2006.01)

(52) U.S. Cl.
CPC ......... *A61K 47/26* (2013.01); *A61M 37/0015* (2013.01); *B29C 43/021* (2013.01); *B29C 43/52* (2013.01); *C12N 7/00* (2013.01); *A61K 2039/522* (2013.01); *A61K 2039/5254* (2013.01); *A61K 2039/54* (2013.01); *A61K 2039/55511* (2013.01); *A61M 2037/003* (2013.01); *A61M 2037/0053* (2013.01); *B29C 2043/561* (2013.01); *B29K 2005/00* (2013.01); *B29L 2031/7544* (2013.01); *C12N 2760/16034* (2013.01)

(58) Field of Classification Search
CPC .......... A61K 2039/55511; A61K 39/02; A61K 39/145; A61K 47/26; A61M 2037/003; A61M 2037/0053; A61M 37/0015; B29C 2043/561; B29C 43/021; B29C 43/52; B29C 43/56; B29K 2005/00; B29L 2031/7544; C12N 2760/16034; C12N 7/00

See application file for complete search history.

(56) References Cited

U.S. PATENT DOCUMENTS

| | | | |
|---|---|---|---|
| 8,187,799 | B2 | 5/2012 | Tsvetkova et al. |
| 8,536,125 | B2 | 9/2013 | Tsvetkova et al. |
| 2004/0049150 | A1 | 3/2004 | Dalton et al. |
| 2005/0049625 | A1 | 3/2005 | Shaya et al. |
| 2007/0078414 | A1 | 4/2007 | McAllister et al. |
| 2009/0099502 | A1 | 4/2009 | Tokumoto et al. |
| 2009/0187160 | A1 | 7/2009 | McAllister et al. |
| 2009/0234301 | A1* | 9/2009 | Tomono ............ A61M 37/0015 604/272 |
| 2010/0152701 | A1 | 6/2010 | McAllister et al. |
| 2014/0330198 | A1 | 11/2014 | Zhang et al. |
| 2014/0343499 | A1 | 11/2014 | Zhang et al. |
| 2014/0361459 | A1 | 12/2014 | Kato et al. |
| 2017/0057124 | A1* | 3/2017 | Wakamatsu .......... A61M 37/00 |

FOREIGN PATENT DOCUMENTS

| | | |
|---|---|---|
| JP | 4427691 B2 | 3/2010 |
| JP | 2011-156370 A | 8/2011 |
| JP | 5049268 B2 | 10/2012 |
| JP | 5267910 B2 | 8/2013 |
| JP | 5285943 B2 | 9/2013 |
| JP | 5401446 B2 | 1/2014 |
| WO | WO 2013/082418 A1 | 6/2013 |
| WO | WO 2013/129028 A1 | 9/2013 |

OTHER PUBLICATIONS

Extended European Search Report dated May 22, 2017 in Patent Application No. 15806237.2.

\* cited by examiner

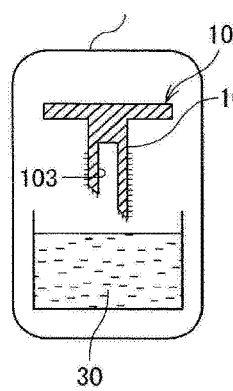
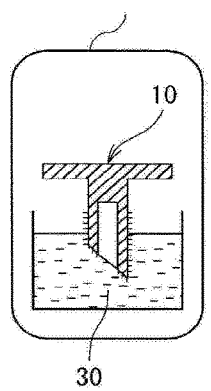
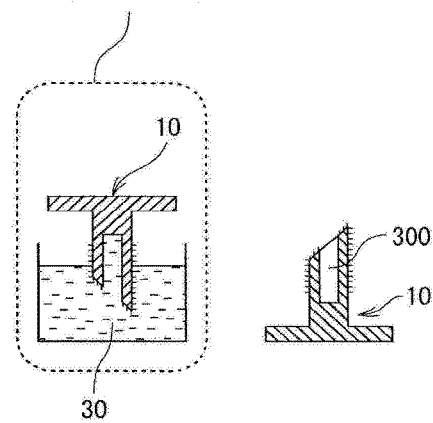
FIG. 3A  FIG. 3B  FIG. 3C  FIG. 3D
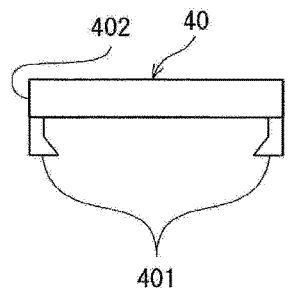
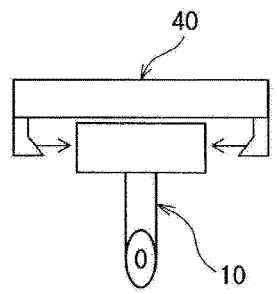
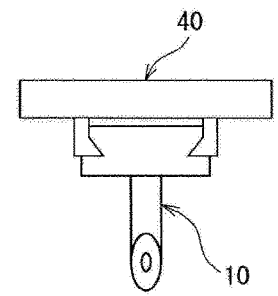
FIG. 4A  FIG. 4B  FIG. 4C

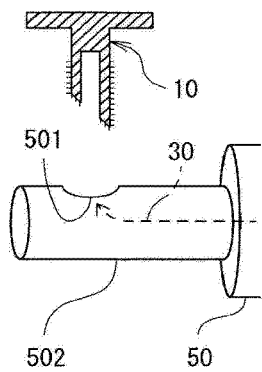
FIG. 6A
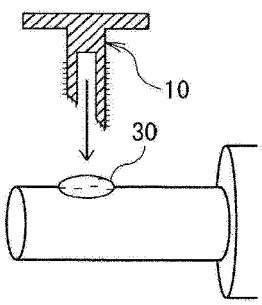
FIG. 6B
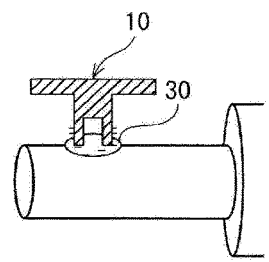
FIG. 6C
FIG. 7A
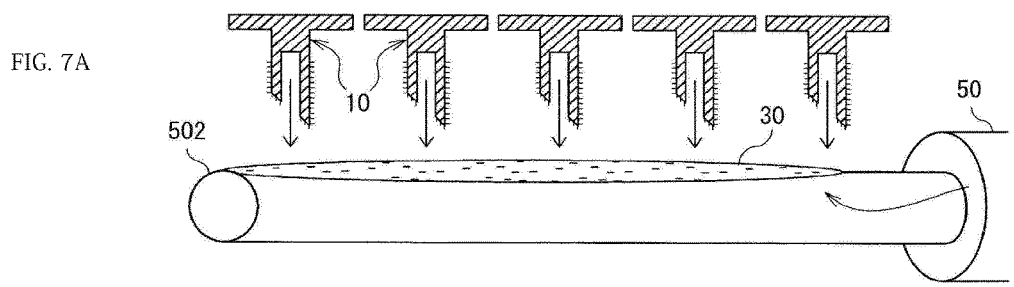
FIG. 7B
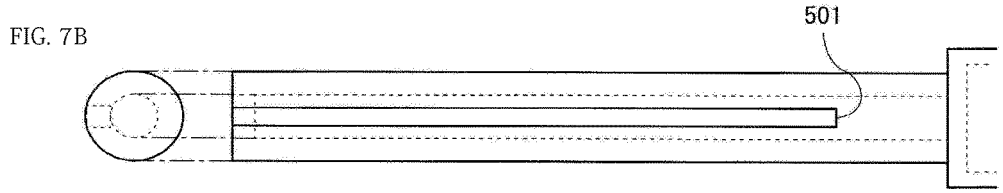

NEEDLE SHAPED BODY AND METHOD FOR MANUFACTURING NEEDLE SHAPED BODY

CROSS-REFERENCE TO RELATED APPLICATIONS

The present application is a continuation of International Application No. PCT/JP2015/002912, filed Jun. 10, 2015, which is based upon and claims the benefits of priority to Japanese Application No. 2014-122515, filed Jun. 13, 2014. The entire contents of these applications are incorporated herein by reference.

BACKGROUND OF THE INVENTION

Field of the Invention

The present invention relates to techniques for needle shaped bodies and more specifically, techniques for needle shaped bodies such as hollow microneedles for transdermal administration of vaccines or the like.

Discussion of the Background

Methods for administering a substance to be delivered into the body in a convenient manner without causing pain include transdermal absorption methods, which allow a substance such as a drug (drug solution) to be delivered into the body by osmosis through the skin. One of the transdermal absorption methods is drug administration by using a microneedle (fine needle) of the order of micrometers that pierces the skin for administration of a drug into the skin (see PTL 1).

Such a fine microneedle is preferably shaped to have a thinness and a tip angle sufficient for piercing the skin and a length sufficient for subcutaneous delivery of a drug solution. For example, the diameter of the microneedle is preferably from several micrometers to several hundreds of micrometers (specifically, approximately in a range from 1 μm to 300 μm) and the length is preferably from several tens of micrometers to several hundreds of micrometers (specifically, approximately in a range from 10 μm to 1000 μm).

In general, a step of manufacturing a microneedle includes a step of forming a microneedle or a through hole by sandblasting, laser processing, microdrilling or the like. Furthermore, there is a proposed method which includes providing an original plate by cutting, forming a reproduced plate from the original plate, and transfer molding by using the reproduced plate (see PTL 2).

Materials that constitute the microneedle are desired to be harmless to the body if the microneedle is left in the body. For example, biocompatible materials such as polylactic acid and hyaluronic acid have been proposed (see PTL 3). For microneedles of a coated type, a method of coating by immersing has been proposed as an example (see PTL 4).

On the other hand, proteins such as enzymes, antibodies and peptides which are widely used for pharmaceutical products are desired not to lose physiological activity during manufacturing processes and storage periods. In particular, when proteins which are polymers are provided in the form of an aqueous solution, there is a problem that the physiological activity cannot be preserved for a long period of time. In such a case, they are stored in a dried state.

Drying methods includes spray-drying, freeze-drying and the like. Spray-drying is a method of instantaneously producing a dry powder by spraying fine liquid droplets into hot air. This method is advantageous for continuous and mass production with low yield loss, and reduces the cost. However, spray-dried products produced by a spray-drying method are exposed to hot air during manufacturing processes. Consequently they may have lower quality than freeze-dried products produced by a freeze-drying method.

On the other hand, freeze-drying is a method of producing a dry product by freezing the solution and then subliming the frozen solution under reduced pressure. This method is characteristic in that a product is not exposed to heat and not deteriorated in quality. It seems that the freeze-dry method does not cause change in drug molecular structure due to drying since drying occurs by sublimation of the ice of the frozen drug, and accordingly, the drug can be dried while preserving the activity. The freeze-dry method is typically used for long term preservation of expensive pharmaceutical products or the like considering the freezing and drying steps which are of high cost and duration.

Although most proteins have characteristics that easily lose activity when exposed to heat, the freeze-dry method can stabilize proteins without applying heat. Accordingly, the freeze-dry method, which removes volatile substances such as water from the drug solution, is advantageously used for accommodating pharmaceutical substances as drugs with high stability and reliability.

Solid injectable preparations used in light of the above are dissolved or suspended in physiological saline or the like when in use. Accordingly, it is known that use of a syringe (injection syringe) as a container for freeze-drying of the injection preparation is advantageous in that transferring of the freeze-dried drug is not necessary (see PTL 5).

The freeze-dried preparation, when used as aqueous solution, has a complication problem that an aqueous solution in which the protein preparation is adjusted to a necessary concentration needs to be prepared each time. For that reason, in freeze-drying of pharmaceuticals of polymers such as proteins and peptides, a saccharide is typically added as a stabilizing agent. For example, a technique of stabilizing proteins by using a saccharide-containing aqueous solution or a saccharide-containing buffer solution is disclosed (see PTL 6).

PTL 1: JP-B-4427691
PTL 2: JP-B-5285943
PTL 3: JP-B-5267910
PTL 4: JP-B-5049268
PTL 5: JP-A-2008-67982
PTL 6: JP-B-5401446

SUMMARY OF THE INVENTION

According to one aspect of the present invention, a method of manufacturing a needle shaped body includes forming on a surface of a substrate a needle shaped portion having a bottomed hole that extends from a tip to the substrate, contacting the tip of the needle shaped portion with a surface of a liquid in an atmosphere at a first pressure lower than atmospheric pressure, increasing the first pressure to a second pressure while the tip is in contact with the surface of the liquid such that the liquid is filled into the bottomed hole, and freeze-drying the liquid filled in the bottomed hole.

According to another aspect of the present invention, a needle shaped body includes a needle shaped portion positioned on a surface of a substrate and including a bottomed hole that extends from a tip to the substrate. The bottomed hole is filled with a freeze-dried liquid, and the needle shaped portion satisfies formulas (1) to (3):

$$0.3 \text{ mm} \leq H \leq 3 \text{ mm} \tag{1}$$

$$1 \leq (H/A) \leq 8 \tag{2}$$

$$1/4 \leq (D/A) \leq 5 \tag{3},$$

where H is a height of the needle shaped portion from the substrate to the tip, A is a maximum diameter of a cross section of the needle shaped portion perpendicular to an axis of the needle shaped portion, and D is a depth of the bottomed hole.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A and 1B are views which explain a needle shaped body according to an embodiment of the present invention, in which FIG. 1A is a perspective view and FIG. 1B is a sectional view.

FIGS. 3A-3D are explanatory views of a method for filling and freeze-drying a drug in the needle shaped body according to an embodiment of the present invention.

FIGS. 4A-4C are explanatory views of an immersing jig for the needle shaped body according to an embodiment of the present invention.

FIGS. 6A-6C are explanatory views of the immersing jig for the needle shaped body according to an embodiment of the present invention.

FIGS. 7A and 7B are explanatory views of the immersing jig for the needle shaped body according to an embodiment of the present invention.

DESCRIPTION OF THE EMBODIMENTS

Figure 1A:
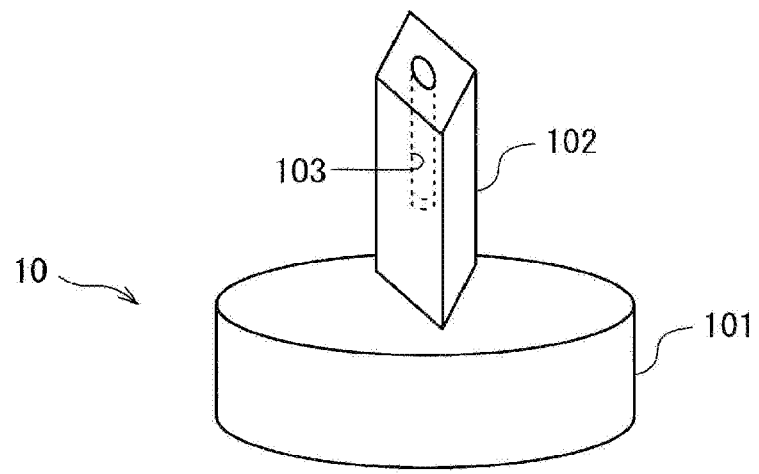

The embodiments will now be described with reference to the accompanying drawings, wherein like reference numerals designate corresponding or identical elements throughout the various drawings.

With reference to the drawings, embodiments of the present invention will be described.

The following describes a needle shaped body according to the present invention and a method for manufacturing the needle shaped body. In this embodiment, a hollow microneedle having a non-through hole (bottomed hole) is shown as an example of the needle shaped body. The hollow microneedle is filled with a drug (drug solution), which is then freeze-dried.

The drawings are schematic, and the dimensions and ratios of components are not to scale. Further, embodiments described below are exemplary configurations that embody the technical idea of the present invention, and do not limit the technical idea of the present invention to the materials, shapes and configurations of components described below. Various modifications can be made to the technical idea of the present invention within the technical scope of claims.

<Needle Shaped Body>

First, a needle shaped body of the present embodiment will be described. The needle shaped body is manufactured, for example, by a method described below.

Figure 1B:
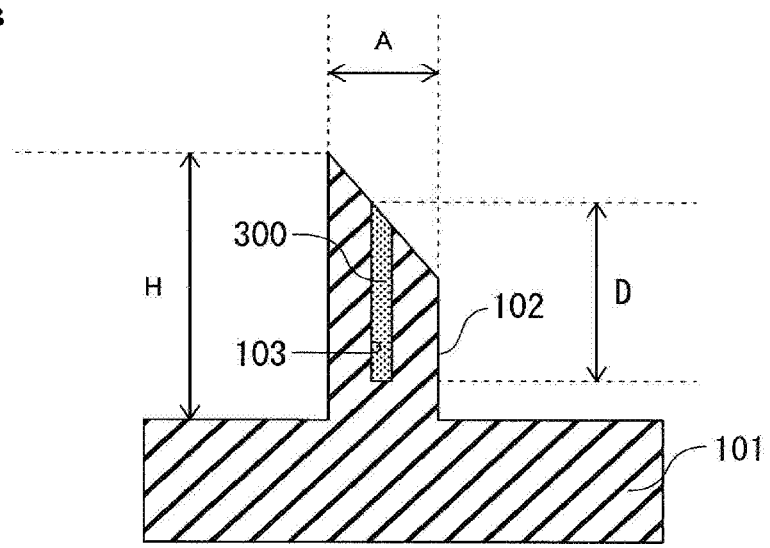

As shown in FIGS. 1A and 1B, the needle shaped body of the present embodiment includes a needle shaped portion 102 which is a needle shaped structure on one surface of a substrate 101. The needle shaped portion 102 includes a hollow hole 103 formed by a bottomed hole which extends from a tip to the substrate 101. As shown in FIG. 1B, the hollow hole 103 is filled with a freeze-dried drug 300. Although FIG. 1B shows that the freeze-dried drug 300 is filled to the bottom of the hollow hole 103, the freeze-dried drug 300 may not be necessarily filled to the bottom of the hollow hole 103.

Further, in the needle shaped body according to an embodiment of the present invention, the number of the needle shaped portion 102 formed on each substrate 101 is not limited to one. A plurality of needle shaped portions may be formed on the substrate. A plurality of needle shaped portions allows for more freeze-dried drug to be released into the skin. Moreover, the needle shaped portion 102 does not necessarily stand perpendicular to a surface of the substrate 101.

Figure 2A:
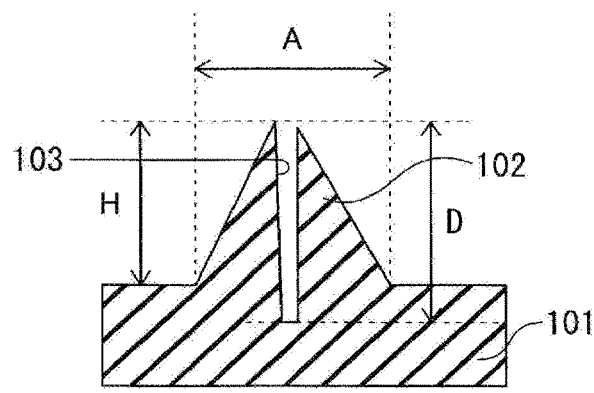
FIGS. 2A-2D are cross sectional views which show examples of other shapes of a needle shaped portion according to an embodiment of the present invention.
Figure 2B:
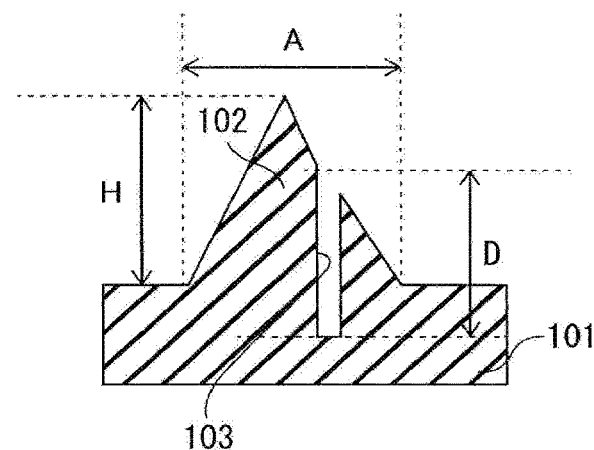
Figure 2C:
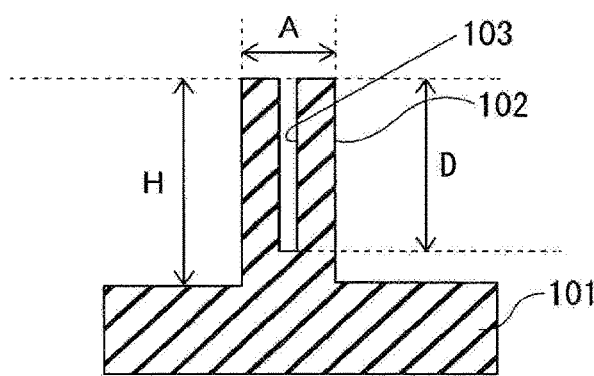
Figure 2D:
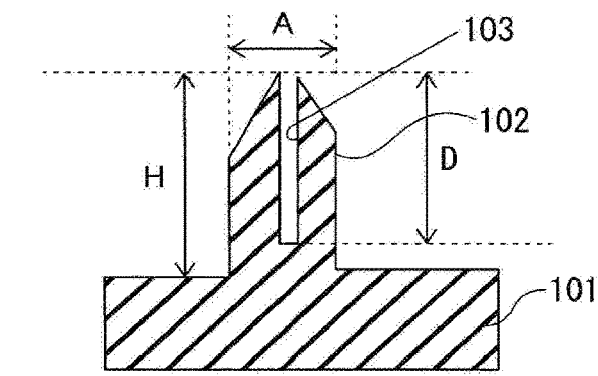

FIGS. 1A and 1B illustrate a needle shaped portion 102 having a rectangular prism shape. The needle shaped portion 102 may be in a columnar shape including a cylindrical shape or a prism shape such as a rectangular prism shape. Alternatively, as shown in FIGS. 2A and 2B, the needle shaped portion 102 may be in a pyramidal shape including a conical pyramid or a rectangular pyramid. Further, the tip of the columnar shape of the needle shaped portion 102 may be truncated as shown in FIGS. 1A and 1B or may not be truncated as shown in FIG. 2C. Moreover, the needle shaped portion 102 may be in a pencil-like shape as shown in FIG. 2D, in which a columnar shape and a pyramidal shape are stacked on the substrate 101 in this order. Alternatively, the needle shaped portion 102 may be in the form in which a pyramidal shape and a columnar shape are stacked on the substrate 101 in this order.

In addition, as shown in FIG. 2B, the hollow hole 103 may be formed at a position eccentric from a center axis of the needle shaped portion 102. In other words, the hollow hole 103 may be any shape of a bottomed hole which extends from the tip of the needle shaped portion 102 to the substrate 101. In FIGS. 2A-2D, illustration of the freeze-dried drug 300 is omitted.

As shown in FIGS. 1A and 1B, when a height of the needle shaped portion 102 from a surface of the substrate 101 to a tip of the needle shaped portion 102 is defined as H, a maximum diameter of a cross section of the needle shaped portion 102 perpendicular to the axis of the needle shaped portion 102 is defined as A, and a depth of the bottomed hole which forms the hollow hole 103 is defined as D, the following formulas (1) to (3) are preferably satisfied:

$$0.3 \text{ mm} \leq H \leq 3 \text{ mm} \tag{1}$$

$$1 \leq (H/A) \leq 8 \tag{2}$$

$$1/4 \leq (D/H) \leq 5 \tag{3}$$

When the height (H) of the needle shaped portion 102 is less than 0.3 mm, puncture of the needle shaped portion 102 into the skin may be difficult. On the other hand, if the height (H) of the needle shaped portion 102 is more than 3 mm, puncture of the needle shaped body may cause severe pain to a subject due to puncture of the needle shaped body into the skin.

Further, when (H/A) is less than 1, puncture of the needle shaped portion 102 into the skin may be difficult. On the other hand, when (H/A) is more than 8, the strength of the needle shaped portion 102 is lowered, which may cause the needle shaped portion 102 to be deformed or broken when the needle shaped body is punctured into the skin.

When (D/H) is less than ¼, releasing of a sufficient amount of the freeze-dried drug 300 may be difficult. On the other hand, when (D/H) is more than 5, a time period to when a sufficient amount of the freeze-dried drug 300 is released in the skin may be longer.

Next, an exemplary method for manufacturing the needle shaped body 10 according to the present embodiment will be described.

<Step of Manufacturing Microneedle>

First, a silicon (Si) substrate such as a monocrystalline silicon wafer with a thickness of 700 μm is provided as the substrate 101 to form a through hole on the silicon substrate by laser processing. A step of forming the through hole is not limited to laser processing, and may also be various known techniques such as wet etching, dry etching, machining and the like. For example, a laser beam can be focused on a processing target such as a silicon substrate so as to form a modified region in the processing target.

After that, the processing target undergoes etching to remove the modified region, thereby forming the through hole which extends in a thickness direction in the silicon substrate.

Next, the silicon substrate is ground by using a grinding device having a diamond blade so as to form a single needle shaped portion 102 with the through hole serving as a center flow path (axis hole). Practically, a plurality of needle shaped portions 102 may be formed. Here, the needle shaped portion 102 is a needle shaped structure having the through hole extending at the center (center axis) with openings of the through hole provided at the tip and a base end (the end close to the substrate 101).

When a surface of the substrate 101 on which the needle shaped portion 102 is formed is defined as a front surface and a surface opposite from the front surface is defined as a rear surface, the substrate 101 which serves as a bottom of the needle shaped portion 102 is the silicon substrate. Accordingly, the rear surface of the substrate 101 can be bonded to a glass substrate by using an anode bonding method. For example, a glass substrate such as soda glass is placed on the rear surface of the substrate 101 so that the interfaces of the glass and the silicon are in contact with each other. Then, while they are heated at approximately 300° C. to 450° C., a high voltage of 500V is applied to the silicon as an anode, thereby allowing easily moving positive ions in the glass to move toward the cathode so as to generate an electrostatically and chemically strong bond between the interfaces of the glass and the silicon. Thus, the substrate 101 and the glass substrate are bonded (joined). The glass substrate may be replaced with a resin. For example, a polyether ether ketone resin may be placed on a rear surface of the substrate 101 to bond the polyether ether ketone resin and the substrate 101 by using an adhesive which contains a thermoplastic resin at the interfaces.

Accordingly, the bonded glass substrate or the resin serves as a cover that covers one end of the through hole, thereby providing a non-through (bottomed) hollow hole 103 formed by the through hole. That is, the needle shaped portion 102 is provided with the hollow hole 103 formed by a bottomed hole which is open to the tip at the center (see FIGS. 1A and 1B).

In addition, another method for manufacturing the needle shaped body 10 may be possible in which the needle shaped portion 102 is manufactured by transfer molding by using a reproduction plate, which is fabricated from the original plate. For example, polydimethylsiloxane (PDMS) solution, which is a thermosetting silicone resin solution, is poured onto the original plate, and a silicon substrate, which is the substrate of the reproduction plate to be transferred, is placed on the PDMS solution. After that, they are heated at 100° C. for a period of 10 minutes for curing the PDMS solution. Then, the original plate is peeled and completely removed, and the PDMS solution is heated at 190° C. for curing (hardening) for a period of 1 hour. Accordingly, a reproduction plate made of PDMS is obtained. In manufacturing of the needle shaped portion 102 by using the obtained reproduction plate, thermal compression molding is performed. The material for the needle shaped portion 102 may be polyglycolic acid (PGA) having a melting point as high as 230° C. PGA is placed on the reproduction plate, heated at 280° C. for melting, and compressed by using a thermal press machine made of a metal for shaping the PGA.

During thermal compression, the reproduction plate and PGA molding material are rapidly cooled to room temperature, promoting separation of the reproduction plate from the PGA. Accordingly, PGA is easily peeled from the reproduction plate. For example, PGA can be easily peeled from the reproduction plate by picking an end portion of PGA which is a microneedle material by using tweezers. Since the substrate 101 and the needle shaped portion 102 are integrally formed of PGA, both are made of PGA. However, practically, a silicon substrate or the like as the substrate 101 may be placed on the reproduction plate after PGA is placed on the reproduction plate. When the needle shaped portion 102 obtained by thermal compression molding is processed with a laser, a non-through (bottomed) hollow hole 103 is obtained. Thus, the needle shaped portion 102 is provided with the non-through (bottomed) hollow hole 103 which is open to the tip and formed at the center.

As described above, the microneedle 10 which includes the needle shaped portion 102 having the non-through and hollow flow path (hollow hole 103) as shown in FIGS. 1A and 1B is obtained. The needle shaped portion 102 of the obtained microneedle 10 is a structure in a columnar shape standing on one surface of the substrate 101 having a tip obliquely truncated and sharpened. In FIGS. 1A and 1B, the illustrated needle shaped portion 102 is formed on the basis of a rectangular prism structure with a tip angle at the truncated surface of the tip of 20.2°, a height of the needle shaped portion 102 of approximately 1400 μm, and a width on one side of the substrate 101 of 500 μm.

The method for manufacturing the above microneedle 10 is not specifically limited. The microneedle 10 can also be manufactured by known methods including machining or micromachining used for manufacturing of semiconductors. In this case, materials for the substrate 101 are not specifically limited and are preferably selected considering processing suitability or availability of the material. For example, such materials include metal materials such as SUS, aluminum and titanium, ceramics such as alumina, aluminum nitride, and machinable ceramics, hard brittle materials such as silicon and glass, and organic materials such as acryl and polyacetal. Known manufacturing methods may be appropriately used depending on the shapes of the microneedle 10 to be manufactured. For example, an original plate having a desired pattern may be fabricated by micromachining technique. Micromachining technique includes, for example, lithography, wet etching, dry etching, sand blasting, laser processing, micromachining or the like. The material for the original plate is not specifically limited, and a material suitable for the microfabrication may be selected.

<Step of Drug Filling>

First, as shown in FIG. 3A, water repellent treatment is provided on at least the tip of the needle shaped portion 102 (except for inside the hollow hole 103) of the substrate 101 in the microneedle 10. Accordingly, as shown in FIGS. 3A-3D, when the tip of the microneedle 10 is brought into contact with the drug solution 30 by using a Z axis control controller or the like, the drug solution 30 can remain only in the hollow hole 103 due to the water repellent effect. The water repellent treatment is preferably provided on a portion other than the center flow path (hollow hole 103) of the needle shaped portion 102 and the surface of the tip (periphery of the opening of the hollow hole 103) of the needle shaped portion 102. The drug solution 30 is required to remain at least inside the hollow hole 103. The water repellent treatment may also be provided on the periphery of the base end (the end close to the substrate 101) of the needle shaped portion 102. Alternatively, when the hollow hole has a sufficient depth (D), the water repellent treatment may be provided only on the periphery of the opening of the hollow hole 103.

The water repellent treatment includes techniques such as super water repelling by plasma treatment, super water repelling by a fluorine surface modifier, super water repelling by chemical adsorption, super water repelling by sol-gel method, super water repellent treatment by electrodeposition coating with addition of fluorine graft copolymer or fluorine resin fine particles, water repelling by silane coupling agent, super water repelling by acrylic silicone/silica composite film, water repelling by chemical adsorption monomolecular film, super water repelling by ion beam modification, and coating of chemical substances having a functional group such as saturated fluoroalkyl group, alkylsilyl group, fluoroacyl group, long chain alkyl group and the like, which can be selected depending on various specimens.

The drug solution 30 may be a drug dissolved or dispersed in a solvent such as water. The drug may be pharmacologically active agents or cosmetic compositions. The drug is appropriately selected depending on the user's application. The pharmacologically active agents include microbes such as influenza vaccine, pain relievers for cancer patients, insulins, biologics, gene therapy agents, injections, oral agents and skin application preparations. Microbes refer to pathogenic viruses, bacteria or microorganisms with attenuated or chemically treated virulence, that is, vaccines.

The drug solution 30 may contain a stabilizer in addition to the drug. In particular, when a microbe is used as a drug, the drug can be stabilized by adding a saccharide to the drug solution. The saccharide added to the drug solution 30 is, for example, a monosaccharide such as inositol, galactose, xylose, glucose, fructose, mannose or ribose, disaccharide such as sucrose, cellobiose, trehalose, maltose or lactose, trisaccharide such as melezitose or raffinose, oligosaccharide such as cyclodextrin, polysaccharide such as dextrin, sugar alcohol such as xylitol, sorbitol, maltitol or mannitol. Of these saccharides, monosaccharides or disaccharides are preferable. In particular, a saccharide selected from glucose, sucrose, trehalose, fructose, lactose or a mixture thereof is more preferable in view of availability.

Figure 5A:
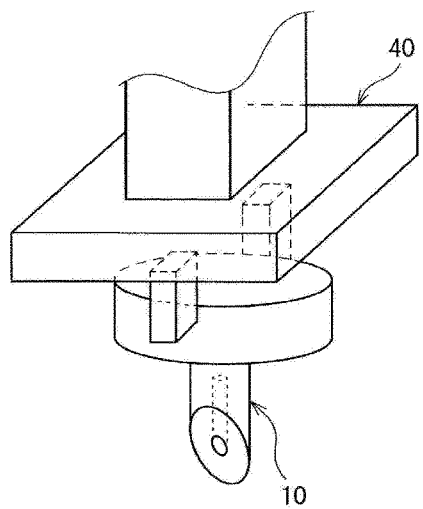
FIGS. 5A and 5B are explanatory views of the immersing jig for the needle shaped body according to an embodiment of the present invention.
Figure 5B:
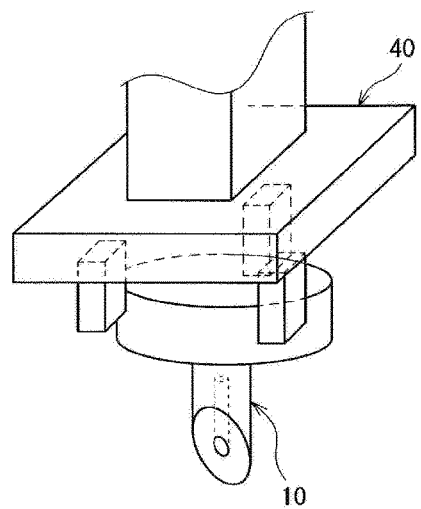
Figure 5C:
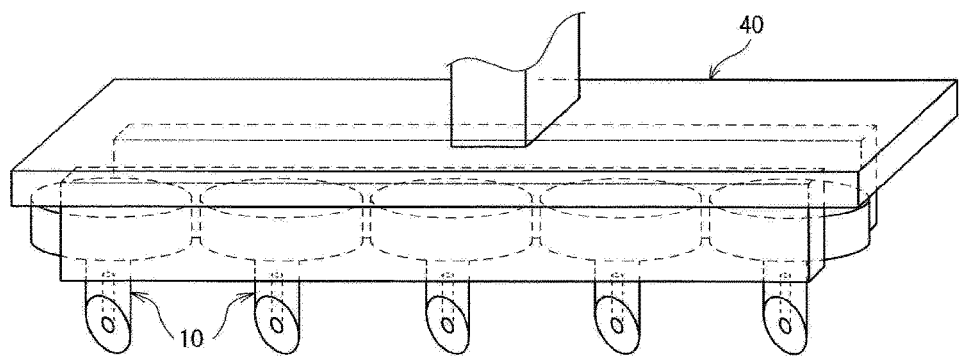
FIG. 5C is an explanatory view of the immersing jig for the needle shaped body according to an embodiment of the present invention.

Further, for accurate immersion, an immersing jig 40 as shown in FIGS. 4A-4C can be used to hold the microneedle and perform numerical control in the axis direction of the needle shaped portion 102 so as to allow only the tip of the needle shaped portion 102 to be in contact with the surface of the drug solution. The axis direction of the needle shaped portion 102 is a Z axis direction in the three dimensional Cartesian coordinate system, having a drug solution surface as an XY plane. The immersing jig 40 can grip (hold) the microneedle 10 by opening and closing a plurality of claws 401 mounted on a support body 402 of the immersing jig 40. For example, the immersing jig 40 is a robot hand or a gripper. The claw 401 can grip the microneedle 10 at two or three points as shown in FIGS. 5A and 5B, or alternatively, can grip a plurality of microneedles 10 as shown in FIG. 5C. The claw 401 temporarily holds the microneedle 10 so that the microneedle 10 is easily released from the immersing jig 40 by an external pressure.

For filling of the drug solution into the hollow hole 103, as shown in FIGS. 3A and 3B, the tip of the needle shaped portion 102 of the microneedle 10 is immersed in the drug solution 30 in a chamber 20 which is decompressed to a first pressure which is lower than atmospheric pressure. Then, as shown in FIG. 3C, the pressure of the chamber 20 is changed to a second pressure (for example, released to atmospheric pressure) which is higher than the first pressure so that the drug solution 30 is filled into the hollow hole 103 which is the bottomed hole. After that, as shown in FIG. 3D, the drug is freeze-dried.

Another example of the filling method is shown in FIGS. 6A-6C, in which a drug solution tank 50 in the decompression chamber 20 (not shown in FIGS. 6A-6C) can be used to fill the drug solution 30 into the hollow hole 103 which is the bottomed hole. The decompression chamber 20 houses the drug solution tank 50 and a pipe 502 having one open end connected to the drug solution tank 50. On a wall of the pipe 502, an opening 501 is formed to communicate with the inside of the pipe 501. The drug solution tank 50 stores the drug solution 30. The opening 501 allows a predetermined amount of the drug solution 30 to flow out therethrough. Further, at least the opening 501 may be disposed inside the decompression chamber 20.

Then, while the needle shaped portion 102 of the microneedle 10 is oriented downward by the immersing jig 40 in the decompression chamber 20, the tip of the needle shaped portion 102 is brought into contact with the drug solution 30 and immersed therein under a reduced pressure (first pressure: decompressed atmosphere) as shown in FIGS. 6A-6C. With the drug solution 30 remaining in the needle shaped portion 102, the first pressure is increased to the second pressure (for example, atmospheric pressure) so that the drug solution 30 is filled into the hollow hole 103.

In filling of the drug solution 30 into the hollow hole 103, the pressure may be adjusted from the first pressure to the second pressure, which is higher than the first pressure. When the second pressure is atmospheric pressure, the pressure can be changed to the second pressure by a simple control.

Moreover, a difference between the first pressure and the second pressure is preferably in a range of 0.02 MPa or more and 0.08 MPa or less. When a difference between the first pressure and the second pressure is less than 0.02 MPa, it may be difficult to fill a sufficient amount of the drug solution 30 into the hollow hole 103. On the other hand, when a difference between the first pressure and the second pressure is more than 0.08 MPa, the liquid surface of the drug solution may ripple, which causes unstable contact between the drug solution and the tip of the needle shaped portion, leading to difficulties in filling of the drug solution 30 into the hollow hole 103.

The opening 501 may be formed in a linear shape as shown in FIGS. 7A and 7B so that the hollow holes 103 of the needle shaped portions 102 of a plurality of microneedles 10 can be immersed simultaneously. In this case, the immersing jig 40 is formed to hold the needle shaped portions 102 which are arranged linearly as shown in FIG. 5C.

Figure 7C:
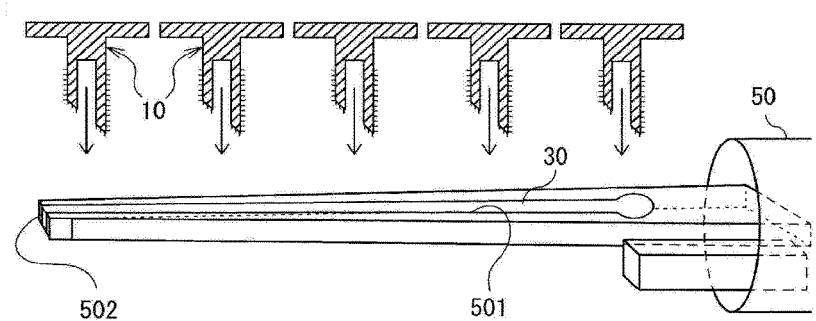
FIGS. 7C and 7D are explanatory views of the immersing jig for the needle shaped body according to an embodiment of the present invention.
Figure 7D:
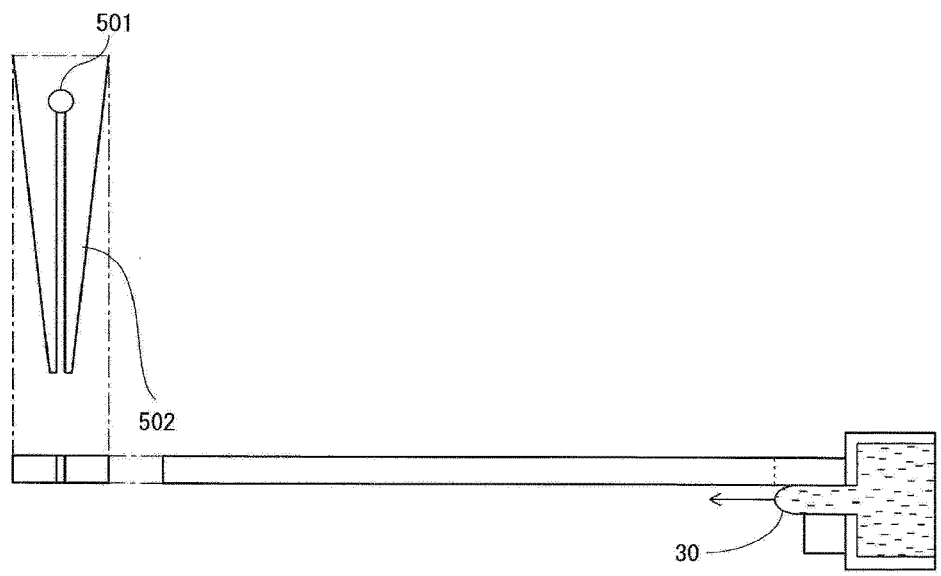

Alternatively, as shown in FIGS. 7C and 7D, the opening 501 may be formed to have a linear slit like a fountain pen tip on a wall of the pipe 502 so that the drug solution 30 is supplied to the opening 501 of the pipe 502 through the linear slit by a capillary effect.

In the step of drug filling, the tip of the needle shaped portion 102 oriented downward can be brought into contact with the liquid surface while the liquid is supplied from above. However, considering stable contact between the needle shaped portion and the liquid, it is preferable to bring the tip of the needle shaped portion oriented downward into contact with the liquid surface as shown in FIGS. 3A-D.

<Step of Freeze-Drying of Drug Solution>

The drug solution 30 filled in the hollow hole 103 of the needle shaped portion 102 of the microneedle 10 is rapidly frozen, for example, by using liquid nitrogen, and then dried under a reduced pressure. In this case, when the temperature of specimen is increased as time elapses, the specimen can be dried in shorter time. Accordingly, it is preferable that the specimen is dried while increasing the temperature of the specimen. For example, the microneedle portion of the microneedle, which is oriented upward, is placed in a freeze-drying machine for drying. Drying is performed under a reduced pressure of 1.33 Pa. Here, the temperature is increased under such conditions that it is increased by 5° C. for every 3 hours from −40° C. to 5° C., and by 10° C. for every 3 hours from 5° C. to 25° C. Then, the dried substance is taken out from the freeze-drying machine, transferred into a desiccator (moisture-proof cabinet) which contains silica gel, left for 7 days, and completely dehydrated to thereby obtain the microneedle 10 having the hollow hole 103 in which the drug solution 30 is filled and freeze-dried.

The obtained microneedle 10 is punctured into the skin by using a finger or a dedicated tool, an applicator (pressing device). After the elapse of a predetermined time, the microneedle 10 is removed from the skin. The applicator is a support tool for fixing the microneedle 10 at a puncture position and an angle to the skin, and is fabricated depending on the shape of the microneedle 10. By use of the applicator, a user can easily recognize puncture of the microneedle 10. Further, by use of the applicator, a user can easily puncture the needle portion of the needle shaped body in a direction vertical to the skin when puncturing the microneedle 10 into the skin. The freeze-dried drug solution 30 is dissolved by a body fluid or the like in the skin (subcutaneously) so as to release the drug in the skin.

In order to protect the freeze-dried drug solution 30, the needle shaped portion 102 or the tip (at least the opening of the hollow hole 103) may be covered by a protective film. For example, the protective film has water resistant (waterproof) properties or moisture resistant properties. Further, the protective film may also have heat resistance, abrasion resistance, oxidation resistance, chemical resistance, contamination resistance or the like. Preferably, the protective film is mounted on the needle shaped portion 102 or the tip (at least on the opening of the hollow hole 103) after the microneedle 10 is manufactured, and detached when the microneedle 10 is in use. However, the protective film is not necessarily limited to the above examples and may be provided for temporary protection of the drug solution 30. That is, the protective film may be formed of a material which is harmless to the body and eluted by a body fluid in the skin (subcutaneously) so that it is punctured along with the microneedle 10 into the skin. Alternatively, the protective film may be formed to cover the entire microneedle 10. For example, the protective film may be a housing container (case) for the microneedle 10.

As described above, the hollow microneedle in which the drug is filled and freeze-dried according to the present embodiment can be manufactured. Further, the hollow microneedle according to the present embodiment and a method for manufacturing the same are not limited to the present embodiment, and also include other known processes which can be expected in each step.

Advantageous Effect of the Present Embodiment

A method for manufacturing the needle shaped body according to the present embodiment is a method for manufacturing a fine needle shaped body, in which the drug is filled and freeze-dried. For example, the needle shaped body is a hollow microneedle having a non-through (bottomed hole) hollow hole. Specifically, a non-through (bottomed) hollow hole which is open at the tip is formed at the center of the needle shaped body by using laser processing. Then, the needle shaped body and the drug solution are placed in a chamber, which is then decompressed. Then, the drug solution is allowed to be filled into the hollow hole by releasing the pressure to the atmosphere in the state that the tip (at least the opening of the hollow hole) of the needle shaped body is in contact with the drug solution. Then, the drug solution in the hollow hole is freeze-dried and fixed thereto.

According to the present embodiment, a non-through (bottomed) hollow hole which is open to the tip is formed at the center of the needle shaped body, the tip (at least the opening of the hollow hole) of the needle shaped body is brought into contact with the liquid surface of the drug solution, and the drug solution is allowed to be filled into the hollow hole by releasing pressure to the atmosphere after previous pressure reduction. Accordingly, the hollow microneedle in which the drug solution is filled and freeze-dried can be manufactured at low cost without a need of providing a large amount of drug solution into the drug solution tank in the chamber (container) while preventing contaminants from entering the hollow microneedle. Further, the drug solution is filled in the hollow hole and then freeze-dried to be fixed thereto. Accordingly, the drug solution fixed to the hollow hole can be dissolved by a body fluid in the skin (subcutaneously) and released when the needle shaped body is punctured into the skin, thereby enabling sustained release.

With the needle shaped body according to an embodiment of the present invention, a desired amount of drug can be filled in the non-through (bottomed hole) hollow hole in a stable manner. Drug filling under reduced compression can prevent air bubbles entrained by the drug solution from entering into the non-through (bottomed hole) hollow hole, compared with the case where the drug solution is filled under atmospheric pressure. Further, compared with the case where the drug solution is filled by suctioning from the substrate of the hollow microneedle having the through hole, the filling amount of drug solution can be prevented from varying.

Microneedles are mainly divided in shape into a hollow type and a solid type. The hollow type is a downsized version of existing injection needles and serves to introduce a drug solution into the body. The solid type is further divided into a coated type and a dissolving type. The coated type has a drug (drug solution) coated on the surface of the microneedle. The dissolving type is formed of a drug and a needle which are integrally formed so that a drug-containing microneedle is dissolved in the skin (subcutaneously) by a body fluid or the like to release the drug in the skin.

In solid coated type microneedles, the coated amount is limited since more than a specific amount of the drug cannot be applied. If the amount of drug to be fixed on a surface of hollow microneedle is increased, the drug solidifies at the tip of the microneedle in a matchstick like shape after it is filled and freeze-dried. Consequently, the tip becomes rounded and loses its acute angle. On the other hand, in solid dissolving type microneedles, the transdermal absorption amount of a drug is limited since the drug of the puncturing needle elutes in the skin only to the height position. Accordingly, the hollow microneedles are preferably used. However, when a drug solution is introduced into a through hole of the hollow microneedles having a through hole, the through hole may be immersed in the drug solution at one end and may be exposed to the outside the drug solution at the other end. In this case, contaminants may enter the through hole from the other end. Further, inside the through hole, the drug solution can be introduced only to the liquid surface of the drug solution. Therefore, the entire hollow microneedle must be immersed in the drug solution, and further, the entire through hole must be filled with drug solution. Accordingly, a large amount of expensive drug solution needs to be prepared in a drug solution tank in a chamber (container) that stores the drug solution to be introduced into the through hole.

An aspect of the present invention is to provide a needle shaped body which includes a needle shaped portion having a hollow hole formed of a bottomed hole, in which drug solution can be filled and freeze-dried while preventing contaminants from entering the hollow hole.

According to an aspect of the present invention, a method for manufacturing a needle shaped body is characterized in that the method includes the steps of: forming a needle shaped portion on one surface of a substrate, the needle shaped portion being a needle shaped structure including a hollow hole formed by a bottomed hole which extends from a tip to the substrate; bringing a tip of the needle shaped portion into contact with a liquid surface of the drug solution under an atmosphere at a first pressure which is lower than atmospheric pressure; filling the drug solution into the hollow hole while the atmosphere is changed from the first pressure to a second pressure which is higher than the first pressure while the tip of the needle shaped portion is in contact with the liquid surface of the drug solution; and freeze-drying the drug solution filled in the hollow hole.

According to another aspect of the present invention, a needle shaped body is characterized in that the needle shaped body includes a needle shaped portion on one surface of a substrate, the needle shaped portion being a needle shaped structure including a hollow hole formed by a bottomed hole which extends from a tip to the substrate, wherein, when a height of the needle shaped portion from the substrate to a tip of the needle shaped portion is defined as H, a maximum diameter of a cross section of the needle shaped portion perpendicular to an axis of the needle shaped portion is defined as A, and a depth of the bottomed hole is defined as D, the needle shaped portion satisfies the following formulas (4) to (6), and the bottomed hole is filled with a freeze-dried drug:

$$0.3 \text{ mm} \leq H \leq 3 \text{ mm} \tag{4}$$

$$1 \leq (H/A) \leq 8 \tag{5}$$

$$1/4 \leq (D/H) \leq 5 \tag{6}$$

According to an aspect of the present invention, drug solution is filled into a non-through hollow hole by bringing the tip of the hollow hole (at least an opening of the hollow hole) into contact with a liquid surface of the drug solution followed by reducing pressure and then releasing pressure to the atmosphere. Accordingly, a hollow microneedle can be manufactured with the freeze-dried drug solution being filled in a portion (at and adjacent to the tip) of the non-through hollow hole while preventing contamination inside the hollow hole at low cost without preparing a large amount of expensive drug solution.

Although the description has been made with reference to a limited number of embodiments, the scope of the invention is not limited thereto, and modifications of the above embodiments on the basis of the above disclosure is obvious to a person having ordinary skill in the art. That is, the present invention may not be limited to the aforementioned embodiments. Design modifications or the like can also be made to the above embodiments on the basis of a knowledge of a skilled person in the art, and such modifications or the like are encompassed within the scope of the present invention.

INDUSTRIAL APPLICABILITY

At the manufacturing site, contaminants can be prevented during introduction of the drug solution into the hollow hole of the hollow microneedle. Further, availability in a clinical medical field is extremely high since quick and painless transdermal drug administration can be achieved by a simple press operation when in use. Moreover, besides the medical field, availability also exists in various fields that require fine hollow microneedles. For example, the invention can be applied to a method for manufacturing a hollow microneedle in which a fine drug is filled and freeze-dried, which is used for MEMS devices, optical members, drug discovery, cosmetics, beauty applications or the like.

While the embodiment of the present invention has been described in detail, the invention is not necessarily limited to the above embodiment. Modifications without departing from the principle of the present invention would be encompassed by the present invention.

REFERENCE SIGNS LIST

10 Microneedle
20 Decompression chamber
30 Drug solution
300 Freeze-dried drug
40 Immersing jig
50 Drug solution tank
101 Substrate
102 Needle shaped portion
103 Hollow hole
401 Claw 402 Support body
501 Opening
502 Pipe Obviously, numerous modifications and variations of the present invention are possible in light of the above teachings. It is therefore to be understood that within the scope of the appended claims, the invention may be practiced otherwise than as specifically described herein.

What is claimed is:

1. A needle shaped body, comprising:
a microneedle comprising a substrate and a needle shaped portion formed on a surface of the substrate such that the needle shaped portion has a bottomed hole that extends from a tip of the needle shaped portion toward the substrate through the needle shaped portion,
wherein the bottomed hole of the needle shaped portion of the microneedle is configured to be filled with a freeze-dried liquid, and the needle shaped portion satisfies 0.3 mm≤H≤3 mm, 1≤(WA)≤8, and ¼≤(D/H)≤5, where H is a height of the needle shaped portion from the substrate to the tip of the needle shaped portion, A is a maximum diameter of a cross section of the needle shaped portion perpendicular to an axis of the needle shaped portion, and D is a depth of the bottomed hole from the tip of the needle shaped portion, and the microneedle is formed such that the needle shaped portion has an angled surface extending to the tip of the needle shaped portion and angled with respect to the surface of the substrate and that the bottomed hole of the needle shaped portion has an opening formed on the angled surface of the needle shaped portion.

2. The needle shaped body of claim 1, wherein the bottomed hole of the needle shaped portion of the microneedle is filled with the freeze-dried liquid, and the freeze-dried liquid includes a microbe and a saccharide.

3. The needle shaped body of claim 2, wherein the saccharide comprises at least one of glucose, sucrose, trehalose, fructose, and lactose.

4. The needle shaped body of claim 1, wherein the height of the needle shaped portion from the substrate to the tip of the needle shaped portion is greater than the depth of the bottomed hole from the tip of the needle shaped portion.

5. The needle shaped body of claim 1, wherein the height of the needle shaped portion from the substrate to the tip of the needle shaped portion is less than the depth of the bottomed hole from the tip of the needle shaped portion.

6. A method of manufacturing a needle shaped body, comprising:
forming a microneedle comprising a substrate and needle shaped portion formed on a surface of the substrate such that the needle shaped portion has a bottomed hole that extends from a tip of the needle shaped portion toward the substrate through the needle shaped portion;
contacting the tip of the needle shaped portion with a surface of a liquid in an atmosphere at a first pressure lower than atmospheric pressure;
increasing the first pressure to a second pressure while the tip of the needle shaped portion of the microneedle is in contact with the surface of the liquid such that the liquid is filled into the bottomed hole; and
freeze-drying the liquid filled in the bottomed hole of the needle shaped portion of the microneedle,
wherein the second pressure is the atmospheric pressure, and the bottomed hole of the needle shaped portion of the microneedle is configured to be filled with a freeze-dried liquid, the needle shaped portion is formed such that the needle shaped portion satisfies 0.3 mm≤H≤3 mm, 1≤(H/A)≤8, and ¼≤(D/H)≤5, where H is a height of the needle shaped portion from the substrate to the tip of the needle shaped portion, A is a maximum diameter of a cross section of the needle shaped portion perpendicular to an axis of the needle shaped portion, and D is a depth of the bottomed hole from the tip of the needle shaped portion.

7. The method of claim 6, wherein the first and second pressures have difference in a range of from 0.02 MPa to 0.08 MPa.

8. The method of claim 6, wherein the liquid is stored in a tank comprising a pipe having an opening portion that allows a flow of the liquid, and the contacting of the tip comprises contacting the tip with the liquid flowing in the opening portion in a chamber at the first pressure.

9. The method of claim 6, further comprising:
applying a water repelling treatment to the tip before the contacting of the tip.

10. The method of claim 9, wherein the contacting is executed while the tip is oriented downward.

11. The method of claim 9, wherein the first and second pressures have difference of from 0.02 MPa to 0.08 MPa.

12. The method of claim 10, wherein the first and second pressures have difference of from 0.02 MPa to 0.08 MPa.

13. The method of claim 6, wherein the contacting is executed while the tip is oriented downward.

14. The method of claim 13, wherein the first and second pressures have difference of from 0.02 MPa to 0.08 MPa.

15. The method of claim 6, wherein the first and second pressures have difference of from 0.02 MPa to 0.08 MPa.

16. The method of claim 6, wherein the liquid is stored in a tank including a pipe having an opening portion that allows a flow of the liquid, and the contacting of the tip comprises contacting the tip with liquid that flows out through the opening portion which is placed in a chamber at the first pressure.

17. The method of claim 6, wherein the microneedle is formed such that the needle shaped portion has an angled surface extending to the tip of the needle shaped portion and angled with respect to the surface of the substrate and that the bottomed hole of the needle shaped portion has an opening formed on the angled surface of the needle shaped portion.

18. A method of manufacturing a needle shaped body, comprising:
forming a microneedle comprising a substrate and needle shaped portion formed on a surface of the substrate such that the needle shaped portion has a bottomed hole that extends from the tip of the needle shaped portion toward the substrate through the needle shaped portion;
contacting the tip of the needle shaped portion with a surface of a liquid in an atmosphere at a first pressure lower than atmospheric pressure;
increasing the first pressure to a second pressure while the tip of the needle shaped portion of the microneedle is in contact with the surface of the liquid such that the liquid is filled into the bottomed hole; and
freeze-drying the liquid filled in the bottomed hole of the needle shaped portion of the microneedle,
wherein the bottomed hole of the needle shaped portion of the microneedle is configured to be filled with a freeze-dried liquid, the needle shaped portion is formed such that the needle shaped portion satisfies 0.3 mm≤H≤3 mm, 1≤(H/A)≤8, and ¼≤(D/H)≤5, where H is a height of the needle shaped portion from the substrate to the tip of the needle shaped portion, A is a maximum diameter of a cross section of the needle shaped portion perpendicular to an axis of the needle shaped portion, and D is a depth of the bottomed hole from the tip of the needle shaped portion, and the microneedle is formed such that the needle shaped portion has an angled surface extending to the tip of the needle shaped portion and angled with respect to the surface of the substrate and that the bottomed hole of the needle shaped portion has an opening formed on the angled surface of the needle shaped portion.

19. The method of claim 18, wherein the height of the needle shaped portion from the substrate to the tip of the needle shaped portion is greater than the depth of the bottomed hole from the tip of the needle shaped portion.

20. The method of claim 18, wherein the height of the needle shaped portion from the substrate to the tip of the needle shaped portion is less than the depth of the bottomed hole from the tip of the needle shaped portion.

* * * * *